US007108860B2

United States Patent
Dueva et al.

(10) Patent No.: US 7,108,860 B2
(45) Date of Patent: Sep. 19, 2006

(54) SUNSCREEN COMPOSITIONS

(75) Inventors: Olga V Dueva, White Plains, NY (US); James P SaNogueira, Suffern, NY (US); Barbara Donovan, Wayne, NJ (US)

(73) Assignee: Playtex Products, Inc., Westport, CT (US)

( * ) Notice: Subject to any disclaimer, the term of this patent is extended or adjusted under 35 U.S.C. 154(b) by 509 days.

(21) Appl. No.: 10/448,745

(22) Filed: May 29, 2003

(65) Prior Publication Data

US 2004/0028709 A1    Feb. 12, 2004

Related U.S. Application Data

(60) Provisional application No. 60/386,317, filed on Jun. 6, 2002.

(51) Int. Cl.
- A61K 8/00 (2006.01)
- A61Q 17/04 (2006.01)
- A61Q 17/00 (2006.01)
- A61Q 19/00 (2006.01)

(52) U.S. Cl. .................. 424/401; 424/59; 424/60; 424/400

(58) Field of Classification Search ........... 424/59, 424/60, 400, 401
See application file for complete search history.

(56) References Cited

U.S. PATENT DOCUMENTS

| | | | |
|---|---|---|---|
| 3,003,063 A | 10/1961 | Mayer | 250/83 |
| 4,481,186 A | 11/1984 | Deckner | 424/59 |
| 4,806,344 A | 2/1989 | Gaskin | 424/59 |
| 4,933,177 A | 6/1990 | Grollier et al. | 424/74 |
| 4,954,332 A | 9/1990 | Bissett et al. | 424/59 |
| 5,116,604 A | 5/1992 | Fogel et al. | 424/59 |
| 5,208,013 A | 5/1993 | Klein | 424/59 |
| 5,306,485 A | 4/1994 | Robinson et al. | 424/59 |
| 5,445,815 A | 8/1995 | Siegfried | 424/59 |
| 5,543,136 A | 8/1996 | Aldous | 424/59 |
| 5,547,659 A | 8/1996 | Rinaldi et al. | 424/59 |
| 5,560,917 A | 10/1996 | Cohen et al. | 424/401 |
| 5,587,150 A | 12/1996 | Deflandre et al. | 424/59 |
| 5,667,765 A | 9/1997 | Hansenne et al. | 424/59 |
| 5,672,337 A | 9/1997 | Ascione et al. | 424/59 |
| 5,676,934 A | 10/1997 | Siegfried | 424/59 |
| 5,725,844 A | 3/1998 | Gers-Barlag et al. | 424/59 |
| 5,770,183 A | 6/1998 | Linares | 424/59 |
| 5,824,323 A | 10/1998 | Fishman | 424/401 |
| 5,863,546 A | 1/1999 | Swinehart | 424/401 |
| 5,961,961 A | 10/1999 | Dobkowski et al. | 424/59 |
| 5,976,560 A | 11/1999 | Han et al. | 424/401 |
| 5,985,251 A | 11/1999 | Gonzenbach et al. | 424/59 |
| 5,989,529 A | 11/1999 | Kaplan | 424/59 |
| 6,007,846 A | 12/1999 | Klar | 424/501 |
| 6,043,204 A | 3/2000 | Kaufman et al. | 510/130 |
| 6,048,517 A | 4/2000 | Kaplan | 424/60 |
| 6,071,501 A | 6/2000 | Robinson | 424/59 |
| 6,090,369 A | 7/2000 | Stewart | 424/59 |
| 6,153,208 A | 11/2000 | McAtee et al. | 424/402 |
| 6,159,453 A | 12/2000 | Avnir et al. | 424/59 |
| 6,162,448 A | 12/2000 | Nguyen et al. | 424/401 |
| 6,165,451 A | 12/2000 | Bringhen et al. | 424/59 |
| 6,190,645 B1 | 2/2001 | SaNogueira et al. | 424/59 |
| 6,197,281 B1 | 3/2001 | Stewart et al. | 424/59 |
| 6,210,658 B1 | 4/2001 | Bonda | 424/59 |
| 6,224,852 B1 | 5/2001 | Morgan et al. | 424/59 |
| 6,238,650 B1 | 5/2001 | Lapidot et al. | 424/59 |
| 6,290,938 B1 | 9/2001 | Tanner et al. | 424/59 |
| 6,322,776 B1 | 11/2001 | Ortega, II et al. | 424/59 |
| 6,338,838 B1 | 1/2002 | Berset et al. | 424/59 |
| 6,342,208 B1 | 1/2002 | Hyldgaard et al. | 424/59 |
| 6,352,685 B1 | 3/2002 | Hoshino et al. | 424/59 |
| 6,355,264 B1 | 3/2002 | Garrison et al. | 424/405 |
| 6,365,630 B1 | 4/2002 | Fisher et al. | 514/559 |
| 6,368,639 B1 | 4/2002 | Farooqi et al. | 424/725 |
| 6,372,234 B1 | 4/2002 | Deckers et al. | 424/401 |
| 6,384,023 B1 | 5/2002 | Singleton et al. | 514/159 |
| 6,395,269 B1 | 5/2002 | Fuller et al. | 424/89 |
| 6,416,748 B1 | 7/2002 | Candau et al. | 424/59 |
| 6,432,389 B1 | 8/2002 | Hansenne et al. | 424/59 |
| 6,433,061 B1 | 8/2002 | Marchant et al. | 524/460 |
| 6,436,374 B1 | 8/2002 | Kurz et al. | 424/59 |
| 6,436,376 B1 | 8/2002 | Hansenne et al. | 424/59 |
| 6,436,377 B1 | 8/2002 | Hansenne et al. | 424/59 |
| 6,458,372 B1 | 10/2002 | Scordamaglia-Crockett et al. | 424/401 |
| 6,458,888 B1 | 10/2002 | Hood et al. | 524/808 |

(Continued)

FOREIGN PATENT DOCUMENTS

| | | |
|---|---|---|
| EP | 0848944 | 11/1997 |
| EP | 0930063 | 12/1998 |
| WO | WO 00/57850 | 7/1999 |

OTHER PUBLICATIONS

European Search Report under Section 18 (3) dated Jun. 3, 2005.

(Continued)

*Primary Examiner*—Shelley A. Dodson
(74) *Attorney, Agent, or Firm*—Ohlandt, Greeley, Ruggiero & Perle, L.L.P.

(57) ABSTRACT

The present invention is directed to a cosmetic composition that has an amount of at least two rheology-modifying agents such that the viscosity of the composition remains stable over a broad temperature range. The compositions of the present invention may also include at least one of the following additional components: sunscreen agent, SPF booster, secondary emulsifier, emollient, moisturizer, humectant, film former/waterproofing agent, bio-active (functional) ingredient, pH adjuster/chelating agent, preservative, fragrance, effect pigment, color additive, or any combinations thereof.

79 Claims, 3 Drawing Sheets

U.S. PATENT DOCUMENTS

| | | | |
|---|---|---|---|
| 6,468,509 B1 | 10/2002 | Lapidot et al. | 424/59 |
| 6,485,712 B1 | 11/2002 | Kim et al. | 424/59 |
| 6,488,915 B1 | 12/2002 | Heidenfelder et al. | 424/59 |
| 6,495,122 B1 | 12/2002 | Fankhauser et al. | 424/59 |
| 6,521,217 B1 | 2/2003 | Luther et al. | 424/59 |
| 2001/0014314 A1 | 8/2001 | Harbeck | 424/70.2 |
| 2001/0026789 A1 | 10/2001 | Richard et al. | 424/59 |
| 2001/0031247 A1 | 10/2001 | Josso et al. | 424/59 |
| 2002/0012640 A1 | 1/2002 | Mohammadi et al. | 424/59 |
| 2002/0028185 A1 | 3/2002 | Fisher et al. | 424/59 |
| 2002/0028875 A1 | 3/2002 | Anderle et al. | 524/591 |
| 2002/0037261 A1 | 3/2002 | Lapidot et al. | |
| 2002/0106337 A1 | 8/2002 | Deckers et al. | 424/59 |
| 2002/0114820 A1 | 8/2002 | Deckers et al. | 424/401 |
| 2002/0197217 A1 | 12/2002 | Kang et al. | 424/59 |

OTHER PUBLICATIONS

A New Thickener/Stabilizer Technology; Cosmetics & Toiletries, vol. 108, No. 5, May, p. 61-67, 1993; Kopolow, Kwak, & Helioff.

Rheox—Waterborne Polysaccharide Thickener; Drug & Cosmetic Industry, No. Cosmetic Product News (Suppl.) Aug. 31, 1998, pp. 11.

Al-Mg-hydroxystearate: New Rheological Additive and Stabilizer; Cosmetics & Toiletries, vol. 106 No: Aug. 1991, pp. 53-54, 56, 58-59; Giulini Chem.

FUCOGEL 1000, The Significance of the Efficacy/smoothness Pair; 1996, pp. 265-274; J. Molina.

Secondary Structural Rheology of a Model Cream; J Soc Cosmet Chem, 1994 45 (2), 77-84; Pena, Lee, & Stearns.

A New Thickener Stabilizer Technology; 1993, 108 (5), 61-67; Kopolow, Kwak, & Helioff.

Al-MG-Hydroxystearate: A New Rheological Additive and Stabilizer 1991, Cosmet Toiletries, 106 (8), 53-59.

Cosmetic Lipogels Made From Aluminum-Magnesium-Hydroxy-Stearate, 1990 16th Congress of the IFSCC: Cosmetic Science in the 1990's and Beyond.

The NY Hilton, NYC, USA, Oct. 8-11, 1990, vol. 2, 456-467; U. Assmus.

SUNSCREEN COMPOSITIONS

RELATED APPLICATION

This application claims priority from the U.S. provisional patent application bearing Application Ser. No. 60/386,317, filed on Jun. 6, 2002, now abandoned.

BACKGROUND OF THE INVENTION

1. Field of the Invention

The present invention relates to cosmetic compositions that have enhanced rheological properties. More particularly, the present invention relates to sunscreen compositions that have enhanced rheological properties before and after application.

2. Description of the Prior Art

Cosmetic compositions, including sunscreens, are commercially available in various forms, such as lotions, creams, gels, and the like and are well known in the art. These compositions are typically formulated to have optimal rheological properties at or close to room temperature. One major drawback with these compositions is that they degrade rheologically at elevated temperatures, especially above room temperature. At these elevated temperatures, it has been found that the compositions no longer maintain the desired viscosity, resulting in a product that undesirably may drip or run during dispensing and/or application.

While all cosmetic compositions may be exposed to elevated temperatures, sunscreen compositions are especially susceptible to exposure to elevated temperatures due to the nature of their use. Sunscreen compositions are applied to the skin to protect the skin from the sun's ultraviolet rays that can lead to erythema, a reddening of the skin also known as sunburn. Sunlight or ultraviolet radiation in the UV-B range has a wavelength of 290 nm to 320 nm and is known to be the primary cause of sunburn. Ultraviolet rays at a wavelength of 320 nm to 400 nm, known as UV-A radiation, produces tanning of the skin. However, in the process of doing so, the UV-A rays can damage or harm the skin.

Besides the immediate malady of sunburn, excessive sunlight exposure can lead to skin disorders. For instance, prolonged and constant exposure to the sun may lead to actinic keratoses and carcinomas. Another long-term effect is premature aging of the skin. This condition is characterized by skin that is wrinkled, cracked and has lost its elasticity.

As stated above, sunscreens are typically formulated with the goal of inhibiting skin damage from the sun's rays. The sunscreen composition filters or blocks the harmful UV-A and UV-B rays that can damage and harm the skin. It is believed that sunscreen agents accomplish this by absorbing the UV-A and/or UV-B rays.

Consumers consider many factors when purchasing a sunscreen product, such as, the sun protection factor (SPF), how durable the product is after applying it over the skin, the shelf life of the product, and product form (i.e., lotions, gels, creams, and sprays). Another important and influential property of a sunscreen product considered by a consumer is how the product dispenses and how well the product spreads over the skin. Typically, consumers want a sunscreen that does not drip and/or run from the dispenser orifice, from the hand during application, or once applied to the skin. However, when exposed to the sun or elevated temperatures, typically sunscreen viscosities significantly decrease. This causes the sunscreen to drip and run from both the orifice of the dispenser and on the skin, making it very difficult for a user to evenly apply the sunscreen to the skin. In addition, the viscosity breakdown may result in a loss of product aesthetics, thus the product does not have a smooth, silky feel when applied to the skin, which is another important factor considered by consumers.

The cosmetic compositions of the present invention overcome the prior art deficiencies by providing a composition with a stable viscosity over a broad temperature range. As a result, the composition does not drip or run when dispensed and/or applied to the skin. In addition, the composition imparts an enhanced soft, silky feel when applied.

SUMMARY OF THE INVENTION

It is an object of the present invention to provide a cosmetic composition that can be effectively applied as a lotion, cream or gel.

It is another object of the present invention to provide such a cosmetic composition that has a stable viscosity over a broad range of temperatures.

It is still another object of the present invention to provide such a cosmetic composition that dispenses at elevated temperatures without dripping or running from the orifice of the dispenser.

It is a further object of the present invention to provide such a cosmetic composition that does not drip or run upon application to the skin at elevated temperatures.

It is still a further object of the present invention to provide such a cosmetic composition that has a soft, silky feel and spreads uniformly over the skin.

It is yet another object of the present invention to provide such a cosmetic composition that is a sunscreen composition.

It is still another object of the present invention to provide such a sunscreen composition that is a stable oil-in-water emulsion or gel.

To accomplish the foregoing objects and advantages, the present invention, in brief summary, is a cosmetic composition that has an amount of at least one rheology modifying agent, and more preferably at least two rheology modifying agents, such that the viscosity of the composition remains stable over a broad temperature range. The compositions of the present invention may also include at least one of the following additional components: sunscreen agent, SPF booster, secondary emulsifier, emollient, skin-feel additive, moisturizing agent, humectant, film former/waterproofing agent, bio-active (functional) ingredient, pH adjuster/chelating agent, preservative, fragrance, effect pigment, color additive, or any combinations thereof.

DETAILED DESCRIPTION OF THE INVENTION

Figure 1:
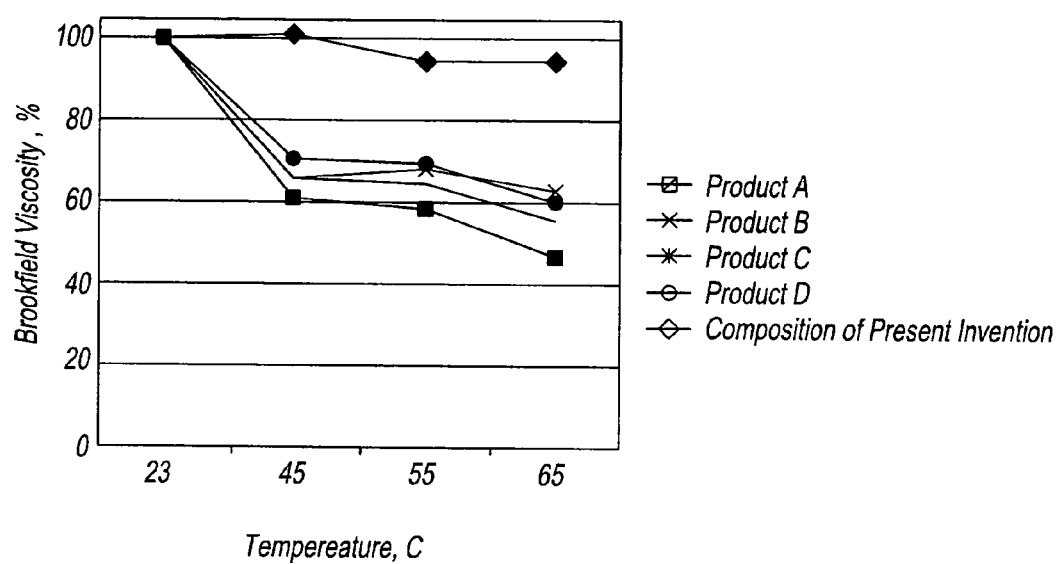
FIG. 1 is a graph of Brookfield viscosity as a function of temperature of a composition according to the present invention as compared to competitive products.

The compositions of the present invention are uniquely formulated to provide not only a stable viscosity over a broad temperature range, but an enhanced feeling of softness and silkiness when the sunscreen composition is applied to the skin. Moreover, the compositions are capable of easy and uniform application over the skin. These enhanced properties are achieved, in large part, by formulating the compositions with an at least one rheology modifying agent, and more preferably two or more rheology modifying agents such that the viscosity remains stable over a broad temperature range.

In addition, the cosmetic compositions may include one or more of the following components: sunscreen agent, SPF booster, secondary emulsifier, emollient, moisturizer, humectant, film former/waterproofing agent, bio-active (functional) ingredient, pH adjuster/chelating agent, preservative, fragrance, effect pigment, color additive or any combinations thereof.

It has been unexpectedly found that the inclusion of two or more rheology modifying agents according to the present invention provides a synergistic effect that results in compositions having a stable viscosity over a broad temperature range. By way of example, the compositions of the present invention unexpectedly exhibit a stable viscosity over a temperature range of about 20° C. to about 70° C.

The term "stable viscosity", as used herein is meant to define a composition having a viscosity that does not deviate more than about 20% from an initially measured viscosity. Preferably, the stable viscosity does not deviate more than 10% from an initially measured viscosity. More preferably, the viscosity does not deviate more than 5% from an initially measured viscosity of a composition of the present invention.

Suitable rheology modifying agents for use in the compositions of the present invention include, but are not limited to, one or more polymeric emulsifiers, thickening agents, synthetic and natural gum or polymer products, polysaccharide thickening agents, stabilizers, associative thickeners, anionic associative rheology modifiers, nonionic associative rheology modifiers, oil-thickening agents, or any combinations thereof. Preferably, the rheology modifying agents are one or more polymeric emulsifiers in combination with one or more thickening agents.

Suitable polymeric emulsifiers for use in the compositions of the present invention include, but are not limited to, acrylates crosspolymer, acrylates/$C_{10-30}$ alkylacrylate crosspolymer, acrylates/vinyl isodecanoate crosspolymer, polyacrylic acid, sodium polymethacrylate, sodium polyacrylate, polyacrylates, or any combinations thereof. Preferably, the polymeric emulsifier is acrylates/$C_{10-30}$ alkylacrylate crosspolymer, acrylates/vinyl isodecanoate crosspolymer, or a combination thereof. The polymeric emulsifiers used as rheological modifying agents assist in building a matrix in the composition.

The amount of emulsifier present in the compositions of the present invention is about 0.01 weight percent (wt. %) to about 10 wt. % of the total weight of the composition. Preferably, the emulsifier is present in an amount about 0.1 wt. % to about 5 wt. % of the total weight of the composition.

Suitable thickening agents that may be used as rheological modifying agents in the compositions of the present invention include, but are not limited to, one or more stabilizers, synthetic and natural gum or polymer products, polysaccharide thickening agents, associative thickeners, anionic associative rheology modifiers, nonionic associative rheology modifiers, oil-thickening agents, acrylates/C10–30 alkylacrylate crosspolymer, acrylates/aminoacrylates/C10–30 alkyl PEG-20 itaconate copolymer, acrylates copolymer, acrylates/steareth-20 methacrylate copolymer, acrylates/beheneth-25 methacrylate copolymer, PEG-150/decyl alcohol/SMDI copolymer, PVP, PVM/MA decadiene crosspolymer, carbomer, PEG crosspolymer, acrylates/palmeth-25 acrylates copolymer, polysaccharides, polyacrylates, polyether-1, sodium magnesium silicates, sodium carbomers, sodium polyacrylates, sodium polymethacrylates, sodium polyacryloyldimethyl taurates, sodium acryloyldimethyl taurate copolymers, sodium carragenan, sodium carboxymethyl dextran, hydroxyethylcellulose, hydroxypropyl cyclodextran, bentonites, trihydroxystearin, aluminum-magnesium hydroxide stearate, xanthan gum, or any combinations thereof. Preferably, the thickening agent is carbomer, sodium carbomer, xanthan gum, or any combinations thereof.

The amount of thickening agent present in the compositions of the present invention is about 0.01 wt. % to about 10 wt. % of the total weight of the composition. Preferably, the thickener is present in an amount about 0.1 wt. % to about 5 wt. % of the total weight of the composition.

It has been unexpectedly found that by including a combination of one or more emulsifiers with one or more thickening agents in a concentration ratio of about 1:10 to about 10:1, preferably about 1:5 to about 5:1, and more preferably about 1:2 to about 2:1, respectively, results in compositions having a stable viscosity over a broad temperature range.

When it is desired to formulate a sunscreen composition, one or more sunscreen agents may be included in the compositions of the present invention. The one or more sunscreen agents that can be used in the present invention must be capable of absorbing or blocking the harmful effects of ultraviolet radiation. In addition, they must be non-toxic and non-irritating when applied to the skin. Suitable sunscreen agents that may be used in the sunscreen composition include, but are not limited to, para-aminobenzoic acid (PABA), butyl methoxydibenzoylmethane (avobenzone), benzophenone-1, benzophenone-2, benzophenone-3, benzophenone-4, benzophenone-6, benzophenone-8, benzophenone-12, bis-ethylhexyloxyphenol methoxyphenyl triazine, methoxycinnamate, ethyl dihydroxypropyl-PABA, glyceryl PABA, homosalate, methyl anthranilate, octocrylene, octyl dimethyl PABA, octyl methoxycinnamate, octyl salicylate, PABA, 2-phenylbenzimidazole-5-sulphonic acid, triethanolamine salicylate, 3-(4-methylbenzylidene)-camphor, red petrolatum, zinc oxide, titanium dioxide, 3-(4-methylbenzyldine)boran-2-one(methylbenzindinecamphor), benzotriazole, octyl triazone, phenylbenzimidazole-5-sulfonic acid, methylene bis-benzotrizolyl tetramethylbutyl phenol, or any combinations thereof.

The one or more sunscreen agents are included in the present composition at about 1 wt. % to about 40 wt. % of the total weight of the composition. The amount of sunscreen agent in the composition will vary in the above range depending on the sun protection factor (SPF) desired. The higher the SPF, the greater the total amount of sunscreen agent. Preferably, the one or more sunscreen agents are included at about 2 wt. % to about 35 wt. % to achieve a SPF of about 2 to about 50. More preferably, the one or more sunscreen agents are included in an amount about 4 wt. % to about 20 wt. % to achieve a SPF value of about 4 to about 30.

The compositions of the present invention also include one or more diluents. Suitable diluents include, but are not limited to, water, glycol or any combinations thereof. Preferably, the diluent is water. The diluent is present in the compositions of the present invention in an amount about 40 wt. % to about 90 wt. %, and preferably about 50 wt. % to about 80 wt. %, of the total weight of the compositions.

In addition to the one or more polymeric emulsifiers, which are primary emulsifiers, one or more secondary emulsifiers may be included in the compositions of the present invention. The one or more secondary emulsifiers are not matrix building emulsifiers, like the primary, polymeric emulsifiers used as the rheological modifying agent. The secondary emulsifier actually reduces particle size in the emulsion of the composition. The one or more secondary emulsifiers suitable for use in the present invention include, but are not limited to, cetyl alcohol, cetearyl alcohol, oleth-10, diethylhexyl esters, sorbitan oleate, sorbitan sesquioleate, sorbitan isostearate, sorbitan trioleate, PEG-20 almond glycerides, polyglyceryl-3-diisostearate, polyglycerol esters of oleic/isostearic acid, polyglyceryl-6 hexaricinolate, polyglyceryl-4-oleate, polygylceryl-4 oleate/PEG-8 propylene glycol cocoate, sodium glyceryl oleate phosphate, hydrogenated vegetable glycerides phosphate, or any combinations thereof.

The amount of secondary emulsifier present in the compositions of the present invention is about 0.01 wt. % to about 5 wt. % of the total weight of the composition. Preferably, one or more additional emulsifiers are present in an amount about 0.05 wt. % to about 2 wt. % and more preferably in an amount about 0.1 wt. % to about 0.5 wt. %, based on the total weight of the composition.

The present compositions may include one or more emollients. An emollient provides a softening, protective or soothing effect on the skin surface and is generally considered safe for topical use. It also helps control the rate of evaporation and the tackiness of the compositions.

A suitable emollient for use in the present compositions include, but is not limited to, cocoglycerides, cyclomethicone, dimethicone, dicapryl maleate, caprylic/capric triglyceride, isopropyl myristate, octyl stearate, isostearyl linoleate, lanolin oil, coconut oil, cocoa butter, olive oil, avocado oil, aloe extracts, jojoba oil, castor oil, fatty acid such as oleic and stearic, fatty alcohol such as cetyl and hexadecyl, diisopropyl adipate, hydroxybenzoate ester, benzoic acid esters of $C_9$–$C_{15}$ alcohols, isononyl iso-nonanoate, alkane such as mineral oil, silicone such as dimethyl polysiloxane, ether such as polyoxypropylene butyl ether and polyoxypropylene cetyl ether, $C_{12}$–$C_{15}$ alkyl benzoate, or any combinations thereof.

The total amount of emollient present in the compositions is typically about 0.1 wt. % to about 30 wt. % of the total weight of the composition. Preferably, emollient is present in an amount about 1 wt. % to about 20 wt. % of the total weight of the composition.

The pH of the compositions of the present invention may be adjusted by one or more pH adjusters and/or chelating agents. For example, sodium hydroxide, triethanolamine, EDTA salt, or any combinations thereof, are suitable pH adjusters/chelating agents that may be included in the sunscreen compositions of the present invention.

An effective amount of a pH adjuster and/or chelating agent is included to adjust the pH of the final composition to about 3 to about 9. Preferably, the pH is adjusted to about 5 to about 8 and more preferably about 6 to about 7.

One or more humectants may be used in the compositions of the present invention. Suitable humectants include, but are not limited to, glycerin, pentylene glycol, hexylene glycol, propylene glycol, butylene glycol, sorbitol, PEG-4, or any combinations thereof.

One or more humectants may be included in the compositions of the present invention in an amount about 0.1 wt. % to about 15 wt. % of the total weight of the composition. Preferably, humectant is present in an amount about 1 wt. % to about 5 wt. % of the total weight of the composition.

The present compositions may include one or more SPF boosters. The SPF booster itself is not an active ingredient, but is designed to enhance the effectiveness of the sunscreen actives present in the formulation. Suitable SPF boosters include, but are not limited to, styrene/acrylates copolymer, sodium bentonite, highly purified white sodium bentonite, montmorillonite, hydrogel, or any combinations thereof. A preferred styrene/acrylates copolymer for use in the present invention is sold under the trade name SunSpheres® by Rohm and Haas Company.

When present, the one or more SPF boosters may be included in the compositions of the present invention in an amount about 1 wt. % to about 6 wt. % of the total weight of the composition. Preferably, SPF booster is present in an amount about 2 wt. % to about 3 wt. % of the total weight of the composition.

Another component that may be used in the compositions of the present invention is a film former/waterproofing agent. The film former/waterproofing agent is a hydrophobic material that imparts film forming and waterproofing characteristics to the emulsion. Suitable film former/waterproofing agent for use in the compositions of the present invention include, but is not limited to, acrylates/acrylamide copolymer, acrylates copolymer, acrylates/$C_{12-22}$ alkylmethacrylate copolymer, polyethylene, waxes, VP/dimethiconylacrylate/polycarbamylpolyglycol ester, butylated PVP, PVP/hexadecene copolymer, octadecene/MA copolymer, PVP/eicosene copolymer, tricontanyl PVP, Brassica Campestris/Aleuritis Fordi Oil copolymer, decamethyl cyclopentasiloxane (and) trimethylsiloxysilicate, or any combinations thereof.

In a preferred embodiment, the film former/waterproofing agent is acrylates/$C_{12-22}$ alkylmethacrylate copolymer sold under the tradename Allianz OPT® by ISP.

One or more film formers/waterproofing agents may be present in the compositions of the present invention in an amount about 0.1 wt. % to about 5 wt. % of the total weight of the composition. Preferably, the one or more film formers/waterproofing agents is present in the compositions of the present invention in an amount about 1 wt. % to about 3 wt. % of the total weight of the composition.

In addition, it has been unexpectedly found that the acrylates/$C_{12-22}$ alkylmethacrylate copolymer may protect the lipids in a user's skin by imparting structure to the epidermal lipids in the skin (stratum corneum) and sebaceous lipids (sebum) and preventing them from depletion. As a result, it is believed that the acrylates/$C_{12-22}$ alkylmethacrylate copolymer may enhance and help to maintain the barrier properties of the lipid barrier in stratum corneum.

Therefore, the compositions of the present invention may exhibit moisturizing and anti-inflammatory properties without a need for including moisturizers and/or anti-inflammatory agents in the compositions.

One or more preservatives may be included in the compositions of the present invention. The preservative protects the compositions from microbial contamination and/or oxidation. As such, the preservative can include an antioxidant. Preservatives, such as diazolidinyl urea, iodopropynyl butylcarbamate, chloromethylisotiazolinone, methylisothiazolinone, vitamin E and its derivatives including vitamin E acetate, vitamin C, butylated hydroxytoluene, butylparaben, ethylparaben, methylparaben, propylparaben, isobutylparaben, phenoxyethanol, or any combinations thereof, may be included as a preservative in a composition of the present invention.

Preferably, in one embodiment of the present invention, the preservative is a combination of phenoxyethanol, methylparaben, ethylparaben, propylparaben, isobutylparaben and butylparaben sold under the tradename Phenonip® by Nipa.

About 0.01 wt. % to about 2 wt. % of preservative may be included in a composition of the present invention. Preferably, one or more preservatives total about 0.5 wt. % to about 1.5 wt. % of the total weight of the composition.

The compositions of the present invention may also have other optional additives including bio-active (functional) ingredients. For instance, one or more plant extracts, fruit extracts, vegetable extracts, algae extracts, sugars, polysaccharides, lipids, proteins, peptides, aminoacids, aminoacid derivatives, absorbents, salicylic acid, alpha and beta hydroxy acids, oil and water soluble vitamins including vitamins A, C, and E and their derivatives, or any combinations thereof, may be included in the sunscreen compositions.

When present, the optional additives may be included in the present composition in an amount about 0.001 wt. % to about 10 wt. %, based on the total weight of the composition.

In one embodiment of the present invention, the components of the present invention may be combined to form stable oil-in-water emulsion sunscreen compositions. The one or more sunscreen agents are preferably incorporated into the oil phase and later combined with water with the help of the one or more emulsifiers. The process used to manufacture the composition of the present invention must be capable of forming a homogeneous composition that can be spread into a film.

In one preferred embodiment of the present invention, a sunscreen composition is formulated with about 2 wt. % to about 12 wt. % of sunscreen agent including octinoxate, octocrylene, or any combination thereof; and a combination of carbomer and acrylates/$C_{10-30}$ alkyl acrylate crosspolymer present in an amount about 0.1 wt. % to about 0.5 wt. % and a ratio of about 1:2 to about 2:1. This composition has been found to have a stable viscosity over a broad temperature range. It has also been found to have an enhanced soft, silky feel when applied to the skin. In addition, this composition has a SPF of at least 15. In a more preferred embodiment, this composition also includes about 1 wt. % to about 2 wt. % of acrylates/$C_{12-22}$ alkylmethacrylate copolymer, which imparts a waterproof property to the composition and unexpectedly imparts moisturizing properties to a user's skin.

In a second preferred embodiment of the present invention, a sunscreen composition is formulated with about 1 wt. % to about 8 wt. % of sunscreen agent including octinoxate, octisalate, or any combination thereof; and about 0.1 wt. % to about 0.5 wt. % of a combination of carbomer and acrylates/$C_{10-30}$ alkyl acrylate crosspolymer present in a ratio of about 1:2 to about 2:1. This composition has been found to have a stable viscosity over a broad temperature range. It has also been found to have an enhanced soft, silky feel when applied to the skin. In addition, this composition has a SPF of at least 8. In a more preferred embodiment, this composition also includes about 1 wt. % to about 2 wt. % of acrylates/$C_{12-22}$ alkylmethacrylate copolymer, which imparts a waterproof property to the composition and unexpectedly imparts moisturizing properties to a user's skin.

In a third preferred embodiment of the present invention, a sunscreen composition is formulated with about 1 wt. % to about 4 wt. % of sunscreen agent; and about 0.1 wt. % to about 0.5 wt. % of a combination of carbomer and acrylates/$C_{10-30}$ alkylacrylate crosspolymer present in a ratio of about 1:2 to about 2:1. The sunscreen agent includes octinoxate, octisalate, or any combination thereof. This composition has been found to have a stable viscosity over a broad temperature range. It has also been found to have an enhanced soft, silky feel when applied to the skin. In addition, this composition has a SPF of at least 4. In a more preferred embodiment, this composition also includes about 1 wt. % to about 2 wt. % of acrylates/$C_{12-22}$ alkylmethacrylate copolymer, which imparts a waterproof property to the composition and unexpectedly imparts moisturizing properties to a user's skin.

In a fourth preferred embodiment of the present invention, a sunscreen composition is formulated with about 1.5 wt. % to about 20 wt. % of one or more sunscreen agents; and a combination of carbomer, xanthan gum and acrylates/$C_{10-30}$ alkyl acrylate crosspolymer present in an amount about 0.1 wt. % to about 0.5 wt. % and a ratio of about 1:2 to about 2:1. The sunscreen agent includes avobenzone, octinoxate, octisalate, oxybenzone, or any combinations thereof. This composition has been found to have a stable viscosity over a broad temperature range. It has also been found to have an enhanced soft, silky feel when applied to the skin. In addition, this composition has a SPF of at least 30.

COMPARATIVE EXAMPLES

Product A contains the following active ingredients: homosalate, octyl methoxycinnamate, octyl salicylate, and oxybenzone and the following inactive ingredients: water, PEG-8, silica dimethyl silylate, cetyl phosphate, acrylates/C10–30 alkyl acrylate crosspolymer, tocopherol (Vitamin E), propylene glycol, methylparaben, propylparaben, disodium EDTA, diazolidinyl urea, triethanolamine, and fragrance.

Product B contains the following active ingredients: homosalate, octyl methoxycinnamate, octyl salicylate, oxybenzone, and avobenzone and the following inactive ingredients: water, PEG-8, benzyl alcohol, cetyl phosphate, acrylates/C10–30 alkyl acrylate crosspolymer, propylene glycol, methylparaben, propylparaben, disodium EDTA, triethanolamine, and silica dimethyl silylate.

Product C contains the following active ingredients: homosalate, octyl methoxycinnamate, octyl salicylate, and oxybenzone, and the following inactive ingredients: water, PEG-8, silica dimethyl silylate, cetyl phosphate, acrylates/C10–30 alkyl acrylate crosspolymer, tocopherol (Vitamin E), propylene glycol, methylparaben, propylparaben, disodium EDTA, diazolidinyl urea, triethanolamine, carbomer, and fragrance.

Product D contains the following active ingredients: octyl methoxycinnamate, octyl salicylate, and oxybenzone, and the following inactive ingredients: water, ethylhexyl palmitate, PEG-8, silica dimethyl silylate, cetyl phosphate, acrylates/C10–30 alkyl acrylate crosspolymer, tocopherol (Vitamin E), propylene glycol, methylparaben, propylparaben, disodium EDTA, diazolidinyl urea, triethanolamine, carbomer, and fragrance.

Product E contains the following active ingredients: octyl methoxycinnamate, octyl salicylate, oxybenzone, and homosalate, and the following inactive ingredients: water, sorbitan isostearate, sorbitol, polyglyceryl-3 distearate, octadecene/MA copolymer, triethanolamine, stearic acid, barium sulfate, benzyl alcohol, dimethicone, aloe barbadensis extract, jojoba oil, tocopherol (Vitamin E), methylparaben, propylparaben, disodium EDTA, diazolidinyl urea, carbomer, and fragrance.

Table 1 below indicates Brookfield viscosity changes of a sunscreen composition according to the present invention as compared to four competitor sunscreen products, namely Products A, B, C and D.

TABLE 1

Brookfield Viscosities

Brookfield Viscosity cps, TB/5 rpm/1 min/Average of 6 measurements/with Helipath/at:

| SAMPLE | 22.5 C (Room t°) | 45° C. | 45° C., % | 55° C. | 55° C., % | 65° C. | 65° C., % |
|---|---|---|---|---|---|---|---|
| Sunscreen Composition of Present Invention | 27,200 (100%) | 27,500 | 1.10% | 25,800 | −5.10% | 25,700 | −5.50% |
| Product A | 25,550 (100%) | 15,500 | −39.30% | 15,000 | −41% | 11,780 | −53.40% |
| Product B | 17,500 (100%) | 11,700 | −33.10% | 12,050 | −31.14% | 10,900 | −37.70% |
| Product C | 24,200 (100%) | 16,000 | −33.90% | 15,900 | −34.30% | 13,600 | −43.80% |
| Product D | 24,250 (100%) | 17,100 | −29.40% | 17,000 | −29.90% | 14,500 | −40.20% |

Figure 2:
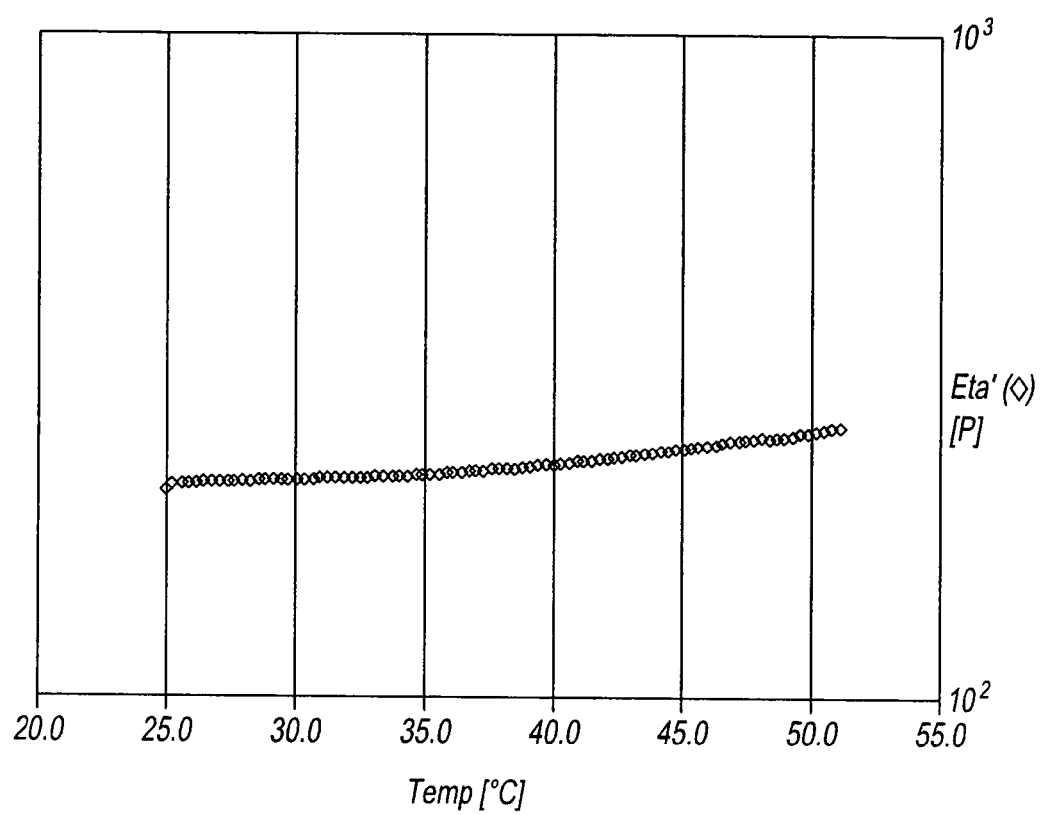
FIG. 2 is a graph of a dynamic temperature ramp of a composition described in the first preferred embodiment of the present invention.
Figure 3:
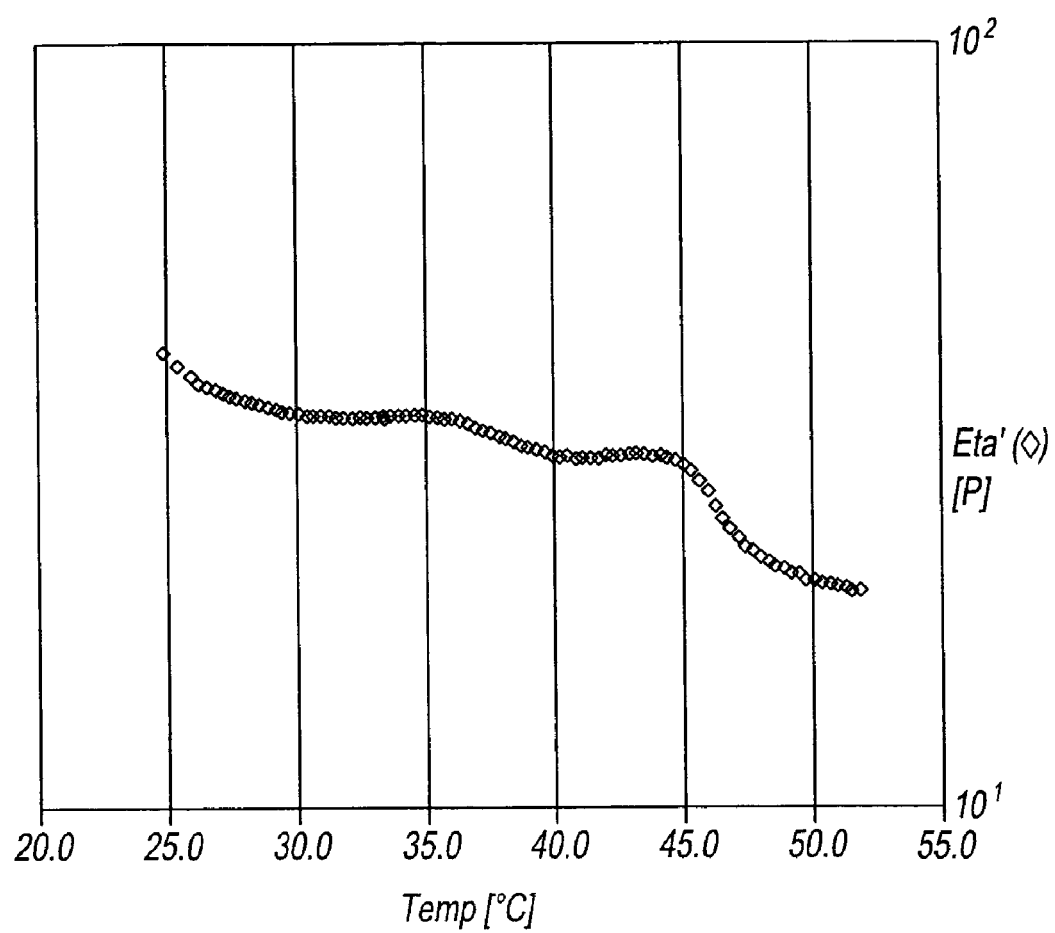
FIG. 3 is a graph of a dynamic temperature ramp of a competitive product.

As is evident from the data set forth above, the composition of the present invention only deviates at most about 5.5% from its original viscosity at room temperature, over a broad temperature range increase, as opposed to the far greater deviation experienced by the competitor products. This critical property of the present invention is also illustrated in FIGS. 1, 2 and 3.

The compositions of the present invention may be prepared according to techniques and methods well known in the art. By way of example, ingredients are incorporated by mixing and applying heat if necessary, until the composition is uniform and homogeneous. The composition may be homogenized to ensure homogeneity and to build the proper viscosity. The sunscreen compositions of the present invention are then packaged as a lotion in any package or container suitable for a sunscreen composition.

Having thus described the present invention with particular reference to preferred embodiments thereof, it will be apparent that various changes and modifications may be made therein without departing from the spirit and scope of the present invention.

What is claimed is:

1. A cosmetic composition having a stable viscosity comprising a first rheological modifying agent and a second rheological modifying agent present in a concentration ratio of about 1:10 to about 10:1, respectively, wherein said stable viscosity deviates from an initial viscosity no more than about 20% over a temperature range of about 20° C. to about 70° C.

2. The composition of claim 1, wherein said concentration ratio is about 1:5 to about 5:1.

3. The composition of claim 1, wherein said concentration ratio is about 1:2 to about 2:1.

4. The composition of claim 1, wherein said first rheological modifying agent is one or more agents selected from the group consisting of polymeric emulsifier, thickening agent, synthetic gum, natural gum, synthetic polymer, natural polymer, polysaccharide thickening agent, stabilizer, associative thickener, anionic associative rheology modifier, nonionic associative rheology modifier, oil-thickening agent, and any combinations thereof.

5. The composition of claim 1, wherein said first rheological modifying agent is one or more polymeric emulsifiers.

6. The composition of claim 5, wherein said one or more polymeric emulsifiers is selected from the group consisting of acrylates crosspolymer, acrylates/$C_{10-30}$ alkylacrylate crosspolymer, acrylates/vinyl isodecanoate crosspolymer, polyacrylic acid, sodium polymethacrylate, sodium polyacrylate, polyacrylates, and any combinations thereof.

7. The composition of claim 1, wherein said second rheological modifying agent is one or more agents selected from the group consisting of polymeric emulsifier, thickening agent, synthetic gum, natural gum, synthetic polymer, natural polymer, polysaccharide thickening agent, stabilizer, associative thickener, anionic associative rheology modifier, nonionic associative rheology modifier, oil-thickening agent, and any combinations thereof.

8. The composition of claim 1, wherein said second rheological modifying agent is one or more thickening agents.

9. The composition of claim 8, wherein said one or more thickening agents is selected from the group consisting of stabilizer, synthetic gum, natural gum, synthetic polymer, natural polymer, polysaccharide thickening agent, associative thickener, anionic associative rheology modifier, nonionic associative rheology modifier, oil-thickening agent, acrylates/C10–30 alkylacrylate crosspolymer, acrylates/aminoacrylates/C10–30 alkyl PEG-20 itaconate copolymer, acrylates copolymer, acrylates/steareth-20 methacrylate copolymer, acrylates/beheneth-25 methacrylate copolymer, PEG-150/decyl alcohol/SMDI copolymer, PVP, PVM/MA decadiene crosspolymer, carbomer, PEG crosspolymer, acrylates/palmeth-25 acrylates copolymer, polysaccharide, polyacrylate, polyether-1, sodium magnesium silicate, sodium carbomer, sodium polyacrylate, sodium polymethacrylate, sodium polyacryloyldimethyl taurate, sodium acryloyldimethyl taurate copolymer, sodium carragenan, sodium carboxymethyl dextran, hydroxyethylcellulose, hydroxypropyl cyclodextran, bentonites, trihydroxystearin, aluminum-magnesium hydroxide stearate, xanthan gum, and any combinations thereof.

10. The composition of claim 1, wherein said first rheological modifying agent is present in an amount about 0.01 wt. % to about 10 wt. % of the total weight of the composition.

11. The composition of claim 1, wherein said first rthelogical modifying agent is present in an amount about 0.1 wt. % to about 5 wt. % of the total weight of the composition.

12. The composition of claim 1, wherein said second rheological modifying agent is present in an amount about 0.01 wt. % to about 10 wt. % of the total weight of the composition.

13. The composition of claim 1, wherein said second rheological modifying agent is present in an amount about 0.1 wt. % to about 5 wt. % of the total weight of the composition.

14. The composition of claim 1, further comprising one or more sunscreen agents.

15. The composition of claim 14, wherein said one or more sunscreen agents are selected from the group consisting of para-aminobenzoic acid, butyl methoxydibenzoylmethane, benzophenone-1, benzophenone-2, benzophenone-3, benzophenone-4, benzophenone-6, benzophenone-8, benzophenone-12, bis-ethylhexyloxyphenol methoxyphenyl triazine, methoxycinnamate, ethyl dihydroxypropyl-PABA, glyceryl PABA, homosalate, methyl anthranilate, octocrylene, octyl dimethyl PABA, octyl methoxycinnamate, octyl salicylate, PABA, 2-phenylbenzimidazole-5-sulphonic acid, triethanolamine salicylate, 3-(4-methylbenzylidene)-camphor, red petrolatum, zinc oxide, titanium dioxide, 3-(4-methylbenzyldine)boran-2-one(methylbenzindinecamphor), benzotriazole, octyl triazone, phenylbenzimidazole-5-sulfonic acid, methylene bis-benzotrizolyl tetramethylbutyl phenol, and any combinations thereof.

16. The composition of claim 14, wherein said one or more sunscreen agents is present in an amount about 1 wt. % to about 40 wt. % of the total weight of the composition.

17. The composition of claim 14, wherein said one or more sunscreen agents are present in an amount about 2 wt. % to about 35 wt. % to achieve a SPF of about 2 to about 50.

18. The composition of claim 14, wherein said one or more sunscreen agents is present in an amount about 4 wt. % to about 20 wt. % to achieve a SPF value of about 4 to about 30.

19. The composition of claim 1, further comprising one or more diluents.

20. The composition of claim 19, wherein said one or more diluents is selected from the group consisting of water, glycols, and any combinations thereof.

21. The composition of claim 19, wherein said one or more diluents is present in an amount about 40 wt. % to about 90 wt. %, of the total weight of the composition.

22. The composition of claim 19, wherein said one or more diluents is present in an amount about 50 wt. % to about 80 wt. %, of the total weight of the composition.

23. The composition of claim 1, further comprising one or more secondary emulsifiers selected from the group consisting of cetyl alcohol, cetearyl alcohol, oleth-10, diethylhexyl esters, sorbitan oleate, sorbitan sesquioleate, sorbitan isostearate, sorbitan trioleate, PEG-20 almond glycerides, polyglyceryl-3-diisostearate, polyglycerol esters of oleic/isostearic acid, polyglyceryl-6 hexaricinolate, polyglyceryl-4-oleate, polygylceryl-4 oleate/PEG-8 propylene glycol cocoate, sodium glyceryl oleate phosphate, hydrogenated vegetable glycerides phosphate, and any combinations thereof.

24. The composition of claim 23, wherein said secondary emulsifier is present in an amount about 0.01 wt. % to about 5 wt. % of the total weight of the composition.

25. The composition of claim 1, further comprising one or more emollients.

26. The composition of claim 25, wherein said one or more emollients is selected from the group consisting of cocoglyceride, cyclomethicone, dimethicone, dicapryl maleate, caprylic/capric triglyceride, isopropyl myristate, octyl stearate, isostearyl linoleate, lanolin oil, coconut oil, cocoa butter, olive oil, avocado oil, aloe extracts, jojoba oil, castor oil, fatty acid, oleic acid, stearic acid, fatty alcohol, cetyl alcohol, hexadecyl alcohol, diisopropyl adipate, hydroxybenzoate esters, benzoic acid esters of $C_9$–$C_{15}$ alcohols, isononyl iso-nonanoate, alkanes, mineral oil, silicone, dimethyl polysiloxane, ether, polyoxypropylene butyl ether, polyoxypropylene cetyl ether, $C_{12}$–$C_{15}$ alkyl benzoate, and any combinations thereof.

27. The composition of claim 25, wherein said one or more emollients is present in an amount about 0.1 wt. % to about 30 wt. % of the total weight of the composition.

28. The composition of claim 1, further comprising one or more pH adjusters.

29. The composition of claim 28, wherein said one or more pH adjusters are selected from the group consisting of sodium hydroxide, triethanolamine, EDTA salts, and any combinations thereof.

30. The composition of claim 1, wherein said composition has a pH about 3 to about 9.

31. The composition of claim 1, further comprising one or more humectants selected from the group consisting of glycerin, pentylene glycol, hexylene glycol, propylene glycol, butylene glycol, sorbitol, PEG-4, and any combinations thereof.

32. The composition of claim 31, wherein said one or more humectants is present in an amount about 0.1 wt. % to about 15 wt. % of the total weight of the composition.

33. The composition of claim 1, further comprising one or more SPF boosters selected from the group consisting of styrene/acrylates copolymer, sodium bentonite, highly purified white sodium bentonite, montmorillonite, hydrogel, and any combinations thereof.

34. The composition of claim 1, further comprising one or more film former/waterproofing agents selected from the group consisting of acrylates/acrylamide copolymer, acrylates copolymer, acrylates/$C_{12-22}$ alkylmethacrylate copolymer, polyethylene, wax, VP/dimethiconylacrylate/polycarbamyl polyglycol ester, butylated PVP, PVP/hexadecene copolymer, octadecene/MA copolymer, PVP/eicosene copolymer, tricontanyl PVP, Brassica Campestris/Aleuritis Fordi Oil copolymer, decamethyl cyclopentasiloxane (and) trimethylsiloxysilicate, and any combinations thereof.

35. The composition of claim 1, further comprising an acrylates/$C_{12-22}$ alkylmethacrylate copolymer.

36. The composition of claim 34, wherein said one or more film formers/waterproofing agents is present in an amount about 0.1 wt. % to about 5 wt. % of the total weight of the composition.

37. The composition of claim 35, wherein said acrylates/$C_{12-22}$ alkylmethacrylate copolymer is present in an amount about 1 wt. % to about 3 wt. % of the total weight of the composition.

38. The composition of claim 1, further comprising one or more preservatives selected from the group consisting of diazolidinyl urea, iodopropynyl butylcarbamate, chloromethylisotiazolinone, methylisothiazolinone, vitamin E and its derivatives, vitamin E acetate, vitamin C, butylated hydroxytoluene, butylparaben, ethylparaben, methylparaben, propylparaben, isobutylparaben, phenoxyethanol, and any combinations thereof.

39. The composition of claim 1, further comprising a preservative comprising a combination of phenoxyethanol, methylparaben, ethylparaben, propylparaben, isobutylparaben and butylparaben.

40. The composition of claim 38, wherein said one or more preservatives is present in an amount about 0.01 wt. % to about 2 wt. % of the total weight of the composition.

41. The composition of claim 30, wherein said preservative is present in an amount about 0.5 wt. % to about 1.5 wt. % of the total weight of the composition.

42. The composition of claim 1, further comprising one or more additives selected from the group consisting of plant extract, fruit extract, vegetable extract, algae extract, sugar, polysaccharide, lipid, protein, peptide, aminoacid, aminoacid derivative, absorbent, salicylic acid, alpha hydroxy acid, beta hydroxy acid, oil soluble vitamin, water soluble vitamin, vitamin A, vitamin A derivative, vitamin C, vitamin C derivative, vitamin E, vitamin E derivative, and any combinations thereof.

43. A sunscreen composition comprising:
about 1 wt. % to about 20 wt. % of sunscreen agent; and
a synergistic combination of a first rheological modifying agent and a second rheological modifying agent,
wherein said composition has a stable viscosity over a temperature range of about 20° C. to about 70° C., and
wherein said stable viscosity deviates from an initial viscosity no more than about 20% over said temperature range.

44. The composition of claim 43, wherein said sunscreen agent is selected from the group consisting of para-aminobenzoic acid, butyl methoxydibenzoylmethane, benzophenone-1, benzophenone-2, benzophenone-3, benzophenone-4, benzophenone-6, benzophenone-8, benzophenone-12, bis-ethylhexyloxyphenol methoxyphenyl triazine, methoxycinnamate, ethyl dihydroxypropyl-PABA, glyceryl PABA, homosalate, methyl anthranilate, octocrylene, octyl dimethyl PABA, octyl methoxycinnamate, octyl salicylate, PABA, 2-phenylbenzimidazole-5-sulphonic acid, triethanolamine salicylate, 3-(4-methylbenzylidene)-camphor, red petrolatum, zinc oxide, titanium dioxide, 3-(4-methylbenzyldine)boran-2-one(methylbenzindinecamphor), benzotriazole, octyl triazone, phenylbenzimidazole-5-sulfonic acid, methylene bis-benzotrizolyl tetramethylbutyl phenol, and any combinations thereof.

45. The composition of claim 43, wherein said first rheological modifying agent is one or more agents selected from the group consisting of polymeric emulsifier, thickening agent, synthetic gum, natural gum, synthetic polymer, natural polymer, polysaccharide thickening agent, stabilizer, associative thickener, anionic associative rheology modifier, nonionic associative rheology modifier, oil-thickening agent, and any combinations thereof.

46. The composition of claim 43, wherein said second rheological modifying agent is one or more agents selected from the group consisting of polymeric emulsifier, thickening agent, synthetic gum, natural gum, synthetic polymer, natural polymer, polysaccharide thickening agent, stabilizer, associative thickener, anionic associative rheology modifier, nonionic associative rheology modifier, oil-thickening agent, and any combinations thereof.

47. The composition of claim 43, wherein said first rheological modifying agent is present in an amount about 0.01 wt. % to about 10 wt. % of the total weight of the composition.

48. The composition of claim 43, wherein said second rheological modifying agent is present in an amount about 0.01 wt. % to about 10 wt. % of the total weight of the composition.

49. The composition of claim 43, wherein said first rheological agent and said second rthelogical agent are present in concentration ratio about 1:10 to about 10:1, respectively.

50. The composition of claim 43, further comprising about 1 wt. % to about 2 wt. % acrylates/$C_{12-22}$ alkylmethacrylate copolymer.

51. The composition of claim 43, further comprising pentylene glycol.

52. A photoprotective composition comprising:
about 2 wt. % to about 12 wt. % of sunscreen agent having octinoxate and octocrylene; and
a synergistic combination of carbomer and acrylates/$C_{10-30}$ alkyl acrylate crosspolymer,
wherein the composition has a stable viscosity over a temperature range of about 20° C. to about 70° C., and
wherein said stable viscosity deviates from an initial viscosity no more than about 20% over said temperature range.

53. The composition of claim 52, wherein said composition has an SPF of at least about 15.

54. The composition of claim 52, wherein said carbomer and said acrylates/$C_{10-30}$ alkyl acrylate crosspolymer are each present in an amount about 0.1 wt. % to about 0.5 wt. %.

55. The composition of claim 52, wherein said carbomer and said acrylates/$C_{10-30}$ alkyl acrylate crosspolymer are present in a concentration ratio of about 1:2 to about 2:1, respectively.

56. A photoprotective composition comprising:
about 1 wt. % to about 8 wt. % of sunscreen agent having octinoxate and octisalate; and
a synergistic combination of carbomer and acrylates/$C_{10-30}$ alkyl acrylate crosspolymer,
wherein the composition has a stable viscosity over a temperature range of about 20° C. to about 70° C., and
wherein said stable viscosity deviates from an initial viscosity no more than about 20% over said temperature range.

57. The composition of claim 56, wherein the composition has an SPF of at least about 8.

58. The composition of claim 56, wherein said carbomer and said acrylates/$C_{10-30}$ alkyl acrylate crosspolymer are each present in an amount about 0.1 wt. % to about 0.5 wt. %.

59. The composition of claim 56, wherein said carbomer and said acrylates/$C_{10-30}$ alkyl acrylate crosspolymer are present in a concentration ratio of about 1:2 to about 2:1, respectively.

60. A photoprotective composition comprising:
about 1 wt. % to about 4 wt. % of sunscreen agent having octinoxate and octisalate; and
a synergistic combination of carbomer and acrylates/$C_{10-30}$ alkyl acrylate crosspolymer,
wherein the composition has a stable viscosity over a temperature range of about 20° C. to about 70° C, and
wherein said stable viscosity deviates from an initial viscosity no more than about 20% over said temperature range.

61. The composition of claim 60, wherein the composition has an SPF of at least about 4.

62. The composition of claim 60, wherein said carbomer and said acrylates/$C_{10-30}$ alkyl acrylate crosspolymer are each present in an amount about 0.1 wt. % to about 0.5 wt. %.

63. The composition of claim 60, wherein said carbomer and said acrylates/C$_{10\text{-}30}$ alkyl acrylate crosspolymer are present in a concentration ratio of about 1:2 to about 2:1, respectively.

64. A photoprotective composition comprising:
about 1.5 wt. % to about 20 wt. % of sunscreen agent having avobenzone, octinoxate, octisalate and oxybenzone; and
a synergistic combination of first rheological modifying agent having carbomer and xanthan gum and a second rthelogical modifying agent having acrylates/C$_{10\text{-}30}$ alkyl acrylate crosspolymer,
wherein the composition has a stable viscosity over a temperature range of about 20° C. to about 70° C., and
wherein said stable viscosity deviates from an initial viscosity no more than about 20% over said temperature range.

65. The composition of claim 64, wherein the composition has a SPF of at least about 30.

66. The composition of claim 64, wherein said first rheological modifying agent and said second rheological modifying agent are each present in an amount about 0.1 wt. % to about 0.5 wt. %.

67. The composition of claim 64, wherein said first rheological modifying agent and said second rheological modifying agent are present in a concentration ratio of about 1:2 to about 2:1, respectively.

68. The composition of claim 1, wherein said stable viscosity deviates over said temperature range no more than about 10%.

69. The composition of claim 1, wherein said stable viscosity deviates over said temperature range no more than about 5%.

70. The composition of claim 43, wherein said stable viscosity deviates from an initial viscosity no more than 10% over said temperature range.

71. The composition of claim 43, wherein said stable viscosity deviates from an initial viscosity no more than 5% over said temperature range.

72. The composition of claim 52, wherein said stable viscosity deviates from an initial viscosity no more than 10% over said temperature range.

73. The composition of claim 52, wherein said stable viscosity deviates from an initial viscosity no more than 5% over said temperature range.

74. The composition of claim 56, wherein said stable viscosity deviates from an initial viscosity no more than 10% over said temperature range.

75. The composition of claim 56, wherein said stable viscosity deviates from an initial viscosity no more than 5% over said temperature range.

76. The composition of claim 60, wherein said stable viscosity deviates from an initial viscosity no more than 10% over said temperature range.

77. The composition of claim 60, wherein said stable viscosity deviates from an initial viscosity no more than 5% over said temperature range.

78. The composition of claim 64, wherein said stable viscosity deviates from an initial viscosity no more than 10% over said temperature range.

79. The composition of claim 64, wherein said stable viscosity deviates from an initial viscosity no more than 5% over said temperature range.

* * * * *